United States Patent
Buerger

(10) Patent No.: US 9,828,578 B2
(45) Date of Patent: Nov. 28, 2017

(54) FERMENTER FOR BIOGAS PLANTS, COMPRISING A SUBMERSIBLE MOTOR-DRIVEN STIRRER VERTICALLY ADJUSTABLE BY MEANS OF A MOTOR

(75) Inventor: Adam Buerger, Haag (DE)

(73) Assignee: UTS BIOGASTECHNIK GMBH, Hallbergmoos (DE)

( * ) Notice: Subject to any disclaimer, the term of this patent is extended or adjusted under 35 U.S.C. 154(b) by 853 days.

(21) Appl. No.: 12/528,723

(22) PCT Filed: Feb. 21, 2008
(Under 37 CFR 1.47)

(86) PCT No.: PCT/EP2008/001372
§ 371 (c)(1),
(2), (4) Date: Dec. 23, 2010

(87) PCT Pub. No.: WO2008/104320
PCT Pub. Date: Sep. 4, 2008

(65) Prior Publication Data
US 2012/0009664 A1 Jan. 12, 2012

(30) Foreign Application Priority Data
Feb. 27, 2007 (DE) .................. 10 2007 009 451

(51) Int. Cl.
*C12M 1/36* (2006.01)
*C12M 1/34* (2006.01)
(Continued)

(52) U.S. Cl.
CPC ............ *C12M 41/44* (2013.01); *C12M 21/04* (2013.01); *C12M 27/02* (2013.01); *Y02E 50/343* (2013.01)

(58) Field of Classification Search
CPC ...... C12M 21/04; C12M 41/44; C12M 27/02; B01D 17/0214; B01D 21/2433;
(Continued)

(56) References Cited

U.S. PATENT DOCUMENTS 3,971,719 A * 7/1976 Peters .................... E21B 43/34
210/104
4,867,872 A * 9/1989 Russell et al. ................ 210/104
(Continued)

FOREIGN PATENT DOCUMENTS

DE 3136345 A1 3/1983
DE 19714342 C1 10/1998
(Continued)

OTHER PUBLICATIONS

EPO Translation of EP 1130084, printed Dec. 2012.*

*Primary Examiner* — William H Beisner
*Assistant Examiner* — Danielle Henkel
(74) *Attorney, Agent, or Firm* — Greer, Burns & Crain, Ltd.

(57) ABSTRACT

A fermenter for biogas plants, including a submersible motor-driven stirrer that can be vertically adjusted by means of a motor. During operation of the biogas plant, the fermenter is filled, to a level, with substrate that is to be fermented, and the agitator blades of the submersible motor-driven stirrer are fully immersed in the substrate. According to the invention, a level gauge is provided, by means of which the level of the substrate is detected and a corresponding level measuring signal is generated as an actual level signal. Furthermore, a control device is provided, to which the level measuring signal is fed and which controls the vertically adjusting motor for the submersible motor-driven stirrer in such a way when a lower level is detected (Continued)

that the stirrer is lowered and the agitator blades continue to be fully immersed in the substrate.

12 Claims, 1 Drawing Sheet

(51) Int. Cl.
*C12M 1/107* (2006.01)
*C12M 1/06* (2006.01)

(58) Field of Classification Search
CPC ..... B01D 21/2488; B01D 21/30; C02F 1/006; G01F 23/0038; G01F 23/296; G01F 23/292; G01F 23/2922; G05D 7/06
USPC ...................................... 435/286.5
See application file for complete search history.

(56) References Cited

U.S. PATENT DOCUMENTS

| | | |
|---|---|---|
| 7,098,669 B2 * | 8/2006 | Carter ........................ 324/605 |
| 2004/0182150 A1 * | 9/2004 | Okada et al. ................. 73/313 |

FOREIGN PATENT DOCUMENTS

| | | | |
|---|---|---|---|
| DE | 19732198 C1 | 10/1998 | |
| EP | 1130084 | * 3/2001 | ............ C12M 1/107 |
| EP | 1256373 A1 | 11/2002 | |
| EP | 1310292 A1 | 5/2003 | |
| EP | 1762607 A1 | 3/2007 | |
| WO | 2004/089523 A1 | 10/2004 | |

* cited by examiner

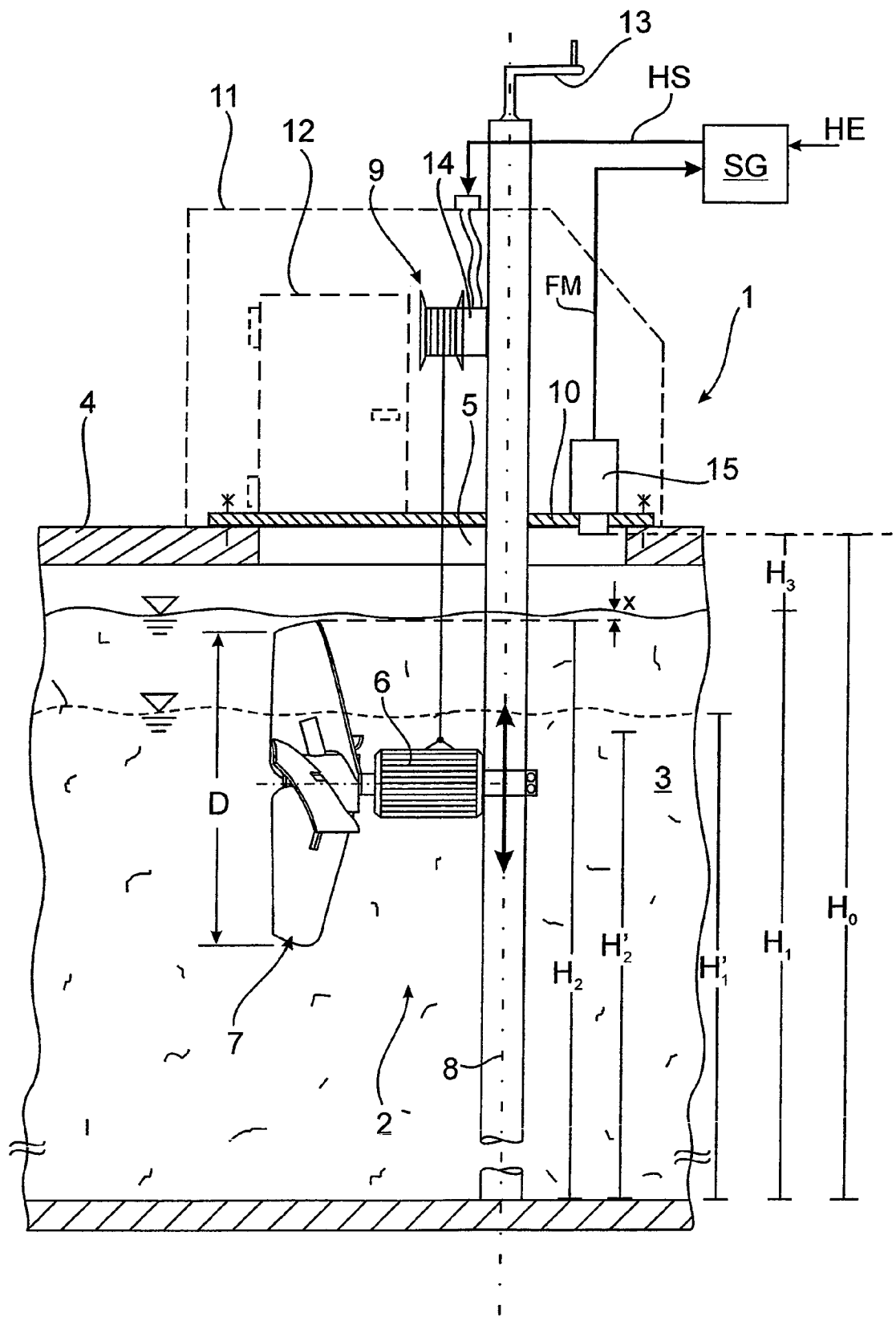

FERMENTER FOR BIOGAS PLANTS, COMPRISING A SUBMERSIBLE MOTOR-DRIVEN STIRRER VERTICALLY ADJUSTABLE BY MEANS OF A MOTOR

BACKGROUND

The invention relates to a biogas plant fermenter comprising a vertically motor-adjustable, submersible motor stirrer.

In biogas plants, fermentation processes take place in which organic matter such as agricultural manure (liquid bovine manure, solid bovine manure, liquid porcine manure, solid porcine manure, liquid chicken manure, dry chicken manure) and/or agricultural residual matter (cut grass beet leaves, silages) and/or agro- or related industrial residual matter (brewer's grains, fruit residual matter, vegetable residual matter, rape meal, cereal residue, slops, molasses) is gasified as a biomass. The gases so generated collect in an upper fermenter tank region of a fermenter tank and can be immediately employed to generate energy, e.g. as a fuel gas for power generation in downstream internal combustion engines with electric generators. For the purpose of fermentation, liquids are added to the organic matter in the fermenter tank wherein the fermentation or gasification process takes place in aerobic or anaerobic conditions by means of microorganisms such as yeasts, bacteria, etc.

One problem arising in these generally known fermentation processes is that the biomass, in particular biomass solids, is not evenly distributed in the fermenter liquid as a rule since for example they rise, accumulating near the liquid surface area. On the other hand there may be the problem of biomass, in particular biomass solids having a higher specific weight than the fermenter liquids, settling down to the fermenter tank bottom where it inconveniently accumulates to form a grit layer. What is generally required for high efficiency of the fermentation process is a highly homogeneous biomass distribution in the fermenter liquid.

To achieve such a highly homogeneous biomass distribution in the fermenter liquid for enhancing efficiency, an agitator device in the relevant category has been known (DE 197 32 198 C1, FIG. 1). This agitator device comprises a submersible motor stirrer which by means of an electric motor-controlled rope winch is held to be height adjustable at an assembly holder arranged vertically in the tank. The submersible motor stirrer comprises a submersible motor having an approximately horizontal agitator shaft at which agitator blades are attached. It is further known from this document to pull out the submersible motor stirrer through a maintenance hole in the fermenter ceiling, up into a servicing well configured dome-shaped for maintenance and/or repairs by means of the rope winch. This is advantageously possible without having to lower the liquid level in the fermenter which would interfere with the fermentation process.

With the plant in operation the submersible motor stirrer is adjusted in height in relation to the stirring requirements by means of actuating the associated height adjustment motor, manually or else to a specified time schedule. The filling level of the fermenter may vary in relation to the course of the fermentation process in conjunction with a usually automated feeding of biomass. In this way, height adjustment of the submersible motor stirrer in the upper fermenter region may cause a state in which the agitator blades emerge at least in part from the substrate during stirring. This will cause the disadvantage of a reduced blending of the substrate and thus a diminished stirring effect, which will on the whole also reduce the biogas yield. Moreover, emerging agitator blades will spray the substrate beyond the substrate level which may soil for example inspection windows. With the agitator blades wholly immersed, the energy consumption of and mechanical load on the submersible motor stirrer are about consistent. In the emerging phase of an agitator blade or part of an agitator blade, however, the mechanical load on this agitator blade decreases and in re-immersing it increases again, such that the drive motor, the bearings and shafts will be subjected to periodically uneven loads. In particular in the case of a substrate having high solid biomass concentration this will increase wear on a submersible stirrer and may considerably reduce its service life.

SUMMARY

Thus it is the object of the invention to improve a biogas plant fermenter in the relevant category having a vertically motor-adjustable submersible motor stirrer such that even in the case of substrate levels varying in operation the stirring effect is consistent in quality while a submersible stirrer is submitted to largely consistent loads.

The fermenter is provided with a filling level gauge to sense the substrate filling level and to generate a corresponding filling level measuring signal as an actual level signal. Moreover a control device is provided to which the filling level measuring signal is transmitted and which, if a lower filling level is sensed which according to pre-settings would cause the agitator blades to emerge, actuates the height-adjusting motor for the submersible motor stirrer so as to lower it far enough for the agitator blades to continue to be totally immersed in the substrate.

According to the invention it is thus automatically ensured even in the case of comparatively high pre-settings of the submersible motor stirrer that the agitator blades are continuously kept immersed even if the substrate level drops in normal operation. Thus the disadvantages discussed above in the case of emerging agitator blades do not occur and a consistent stirring effect is ensured while the submersible motor stirrer is subjected to largely consistent loads.

The filling level gauges employed may be different systems in relation to the fermenter structure and other conditions. Mechanically operating sensors with floaters or displacers in conjunction with position transmitters and limit value switches for generating electrical measurement signals are conceivable. What is particularly suitable is, non-contact filling level gauges having optical and/or acoustic and/or radioactive sensors. In particular one may employ ultrasonic echo-sounder impulse devices above the substrate level, for example in the fermenter cover, or gamma radiators as known per se with counter tube chains with a downstream measuring transducer each to convert the received measurement signal to a corresponding electrical signal. Optionally one may employ filling level gauges as known per se operating hydrostatically by means of a bubbler system.

The present invention further provides a suitable specific arrangement with a sensor of the filling level gauge above the substrate level, preferably at a fermenter cover, so as to detect the free space height ($H_3$) between the non-contact sensor and the substrate level by way of a free space signal (FM). Said free space signal (FM) is transmitted to a control unit (SG) of the control device where the current filling level height $H_1$ is determined by subtraction from the total height ($H_0$) of the fermenter interior by way of $H_1 = H_0 - H_3$. The current filling level height ($H_1$) and a corresponding signal may optionally be determined directly, e.g. by means of a floater arrangement. Via a height adjuster at the control unit or a corresponding signal input, a height adjusting signal (HE) is transmitted to the control unit (SG) corresponding to a desired value ($H_2$) for the submersible apparatus. Said unit actuates the height-adjusting motor by way of a height-adjusting signal (HS) such that the submersible motor stirrer assumes such desired value level ($H_2$) (measured up to the topmost agitator blade tip).

The height control described above is superimposed by the safety control as described below against emergence of the agitator blades: To this end a comparison is performed in the control unit (SG) between the signals of the current filling level ($H_1$) and the desired value level ($H_2$) such that in case that the filling level height ($H_1$) is higher than the desired value level ($H_2$), no further control procedure is carried out but in case that a currently sensed filling level ($H_1$) is lower than the desired value level ($H_2$), the submersible stirrer is lowered down. Lowering down occurs until the current setting height ($H_2'$) of the submersible motor stirrer is lower than the current filling level ($H_1'$) by a height differential amount X. This condition ensures that the agitator blades remain totally immersed including in such operationally lowered substrate filling level. The height differential amount X must be selected such that the agitator blade tips rotate far enough beneath the substrate level for the substrate to not splash and thus securing a consistent stirring action. The height differential amount X can be preset at the control unit (SG) and the superimposed control procedure is carried out for the immersion safeguard of the agitator blades every time an X-value difference is exceeded. Thus it can be ensured that advantageously the control procedure for the immersion safeguard is not continuously active in a critical range but operates in large steps.

Although the control unit (SG) has been described above as a separate apparatus, it may be incorporated in the overall plant control or in part of the plant control with its control function for the immersion safeguard of the agitator blades. Likewise, a filling level gauge may be used for other purposes as well, such as for solids feeding.

A specific embodiment provides for the submersible motor stirrer to be guided at a vertical assembly holder and to be held to be vertically motor-adjustable by means of a rope winch. The motor height adjustment may occur in other ways as known per se, for example at lateral stirrers at which a submersible motor stirrer is arranged at a height-pivotable rocker arm. The rotary actuator motor for a submersible motor stirrer may be an electric, hydraulic, or pneumatic motor.

In a proven arrangement, the assembly holder is accommodated with its upper portion in a dome-shaped servicing well into which the submersible stirrer can be pulled up in particular for maintenance and/or repairs where it is readily accessible.

BRIEF DESCRIPTION OF THE DRAWINGS

The invention will now be described in more detail by way of a drawing.

FIG. 1 is a fragmentary elevation view of an embodiment of the present fermenter.

DETAILED DESCRIPTION

FIG. 1 schematically shows a sectional view of a biogas plant fermenter 1 having an agitator device 2. The fermenter 1 contains a fermentable substrate 3 with liquid and solid biomass contents. Although the present fermenter 1 comprises a concrete cover 4 as the fermenter ceiling, it might be covered with a film roof as known per se. The concrete ceiling is provided with a maintenance and mounting hole 5. The stirring device 2 consists of a submersible motor stirrer 6 with a horizontally oriented agitator shaft where, in the present three-blade arrangement, agitator blades 7 are attached.

The submersible motor stirrer 6 is retained at a vertical assembly holder to be height-adjustable via a rope winch 9.

Above the maintenance and mounting hole 5 covered by a cover plate 10 a servicing well 11 (drawn schematically in dashed lines) mounted gas-tight and having a door 12 is arranged. The assembly holder 8 passes through this servicing well 11 and it can be rotated by a crank 13 for angular adjustment of the submersible motor stirrer 6. Moreover the rope winch 9 is attached at the assembly holder 8 in the upper region of the servicing well 11 such that after removing the cover plate 10 the submersible motor stirrer 6 can be pulled upwardly into the servicing well 11 region for maintenance and repairs. Height adjustment of the submersible motor stirrer 6 occurs by actuating an electrically operated height adjustment motor 14 coupled with the rope winch 9. Actuating occurs through a control unit SG emitting a corresponding height adjustment signal HS to the height adjusting motor 14, for example an electrical stepper motor. The desired height adjustment of the submersible motor stirrer 6 is specified at the control unit SG by way of a height adjusting signal HE. Said height adjusting signal HE may be specified for example manually by way of a manual control or else in the scope of a stirring program with changing height adjustments.

In the presently illustrated case the filling level of the fermenter 1 or the substrate level is shown at $H_1$. The current level adjustment of the submersible motor stirrer 6 (up to the topmost tip of an agitator blade 7 this is the diameter D of the agitator blade arrangement) as preset by the level adjustment signal HE is shown at $H_2$. The agitator blades 7 are obviously totally immersed in the substrate 3 during a stirring function wherein a height differential amount X is maintained between the top agitator blade position and the substrate level.

The fermentation process depends on a plurality of parameters, such as the biomass type, material feed, temperature, intensity of stirring, etc., such that the substrate filling level can noticeably fluctuate during operation. Such operational fluctuation with a lowered substrate level to the filling level $H_1'$ is indicated in dashed lines in the FIGURE. Obviously the agitator blades 7 of the submersible motor stirrer 6 would emerge above the substrate level during stirring in the case of height adjustment $H_2$. To prevent this a filling level gauge 15 is additionally arranged, presently as an ultrasonic echo sounder in the region of the fermenter cover, presently e.g. the cover plate 10 so as to detect the free space height $H_3$ between the filling level gauge 15 and the substrate level, and a corresponding electrical free space height signal FM is transmitted to the control unit SG. There, by means of subtracting the variable free space height $H_3$ from the invariable total height $H_0$, the variable current filling level $H_1$ is determined and captured.

In the case that the filling level $H_1$ is higher than the preset desired value level $H_2$ corresponding to the height adjustment signal HE, the agitator blades 7 are totally immersed for a good stirring effect. In contrast thereto, a superimposed control procedure is carried out if according to the FIGURE the substrate level drops to a height $H_1'$ (shown in dashed lines) such that the agitator blades 7 would then emerge. To this end a comparison is carried out in the control unit between the current height adjustment of the submersible motor stirrer 6, which is captured in the control unit SG, and the currently measured, dropped filling level height $H_1'$. If the dropped filling level height $H_1'$ is lower than the current vertical position of the submersible motor stirrer 6, the control unit SG emits a height adjusting signal HS for a lowering function of the submersible motor stirrer 6 until the current setting height $H_2'$ is again lower than the current filling level height $H_1'$ by a height differential amount X. It is thus automatically ensured that during stirring the agitator blades 7 do not emerge above the substrate level.

The invention claimed is:

1. A biogas plant fermenter comprising:
a cover;
a vertically motor-adjustable, submersible motor stirrer, wherein during operation of the biogas plant, the fermenter is filled to a level ($H_1$) with substrate to be fermented, the submersible motor-driven stirrer with its agitator blades being fully immersed in the substrate;
a filling level gauge attached to said cover and spaced from a top surface of the substrate such that the filling level gauge does not contact the substrate, said filling level gauge being configured to detect the actual filling level ($H_1$) of the substrate by directly measuring the substrate level and generating a corresponding filling level measuring signal as an actual level signal; and
a control device configured to receive the filling level measuring signal and when a lower filling level ($H_1'$) is detected, actuates the height-adjusting motor for the submersible motor stirrer so as to lower it far enough for the agitator blades to continue to be totally immersed in the substrate.

2. The biogas plant fermenter according to claim 1, wherein the filling level gauge comprises a mechanically operating sensor with at least one of a floater and a displacer, each having a position transmitter or a limit value switch.

3. The biogas plant fermenter according to claim 1, wherein the filling level gauge comprises at least one of an ultrasonic echo-sounder impulse device, a non-contact gamma radiator with counter tube chain and a hydrostatic tube for a bubbler system.

4. The biogas plant fermenter according to claim 1, wherein the control device includes a control function incorporated in a plant control.

5. The biogas plant fermenter according to claim 1, wherein the submersible motor stirrer is height-adjustable by means of a motor at a vertical assembly holder and by means of a rope winch.

6. The biogas plant fermenter according to claim 5, wherein the assembly holder is accommodated in the upper region in a dome-shaped servicing well into which the submersible motor stirrer can be displaced upwardly.

7. A biogas plant fermenter comprising:
a cover;
a vertically motor-adjustable, submersible motor stirrer, wherein during operation of the biogas plant, the fermenter is filled to a level ($H_1$) with substrate to be fermented, the submersible motor-driven stirrer with its agitator blades being fully immersed in the substrate;
a filling level gauge attached to said cover and spaced from a top surface of the substrate such that the filling level gauge does not contact the substrate, said filling level gauge being configured to detect the actual filling level ($H_1$) by directly measuring the substrate level and generating a corresponding filling level measuring signal as an actual level signal; and
a control device configured to receive the filling level measuring signal and when a lower filling level ($H_1'$) is detected, actuates the height-adjusting motor for the submersible motor stirrer so as to lower it far enough for the agitator blades to continue to be totally immersed in the substrate,
wherein the filling level gauge includes a sensor and is configured to detect a free space height ($H_3$) between the sensor and the substrate level by way of a free space height signal which is transmitted to a control unit of the control device where by subtraction from the total height ($H_0$) the current filling level ($H_1$)

$$H_1 = H_0 - H_3 \text{ is determined,}$$

wherein via a height adjuster at the control unit a height adjusting signal is transmitted to the control unit corresponding to a desired level value ($H_2$) for the submersible stirrer to actuate the height-adjusting motor by way of a height-adjusting signal such that the submersible motor stirrer assumes such desired value level ($H_2$) measured up to the topmost agitator blade tip,
wherein with a superimposed control as a safety control against the agitator blades emerging, a comparison is performed in the control unit between the signals of the current filling level height ($H_1$) and the desired value level ($H_2$) stored in the control unit, such that when the filling level ($H_1$) is higher than the desired value level ($H_2$), no further control procedure is carried out,
wherein when the currently sensed filling level height ($H_1'$) is lower than the desired value level ($H_2$), an automatic control procedure occurs independently of the preset height adjustment signal, and
wherein the submersible motor stirrer is lowered down far enough until the current setting height ($H_2'$) of the submersible motor stirrer is lower than the current filling level height ($H_1'$) by a height differential amount X such that $$H_1' = H_2' + X$$

and thus the agitator blades are totally immersed in a stirring operation.

8. The biogas plant fermenter according to claim 7, wherein the height differential amount X can be preset at the control unit.

9. The biogas plant fermenter according to claim 7, wherein the superimposed control procedure for the immersion safeguard of the agitator blades is carried out every time as an X-value difference is exceeded.

10. The biogas plant fermenter according to claim 7, wherein the control device includes a control function incorporated in a plant control.

11. The biogas plant fermenter according to claim 7, wherein the submersible motor stirrer is height-adjustable by means of a motor at a vertical assembly holder and by means of a rope winch.

12. The biogas plant fermenter according to claim 11, wherein the assembly holder is accommodated in the upper region in a dome-shaped servicing well into which the submersible motor stirrer can be displaced upwardly.

* * * * *